United States Patent [19]  [11] 4,183,925
Baxter et al.  [45] Jan. 15, 1980

[54] 7-AMINOPHENYLACETAMIDO-Δ³-CEPHEM ANTIBACTERIAL AGENTS AND METHOD OF USE

[75] Inventors: Charles A. R. Baxter, Margate; Braham Shroot, Canterbury, both of England

[73] Assignee: Pfizer Inc., New York, N.Y.

[21] Appl. No.: 844,268

[22] Filed: Oct. 21, 1977

Related U.S. Application Data

[62] Division of Ser. No. 670,880, Mar. 26, 1976, Pat. No. 4,080,451.

[30] Foreign Application Priority Data

Mar. 27, 1975 [GB] United Kingdom ............... 12813/75
Oct. 2, 1975 [GB] United Kingdom ............... 40447/75
Oct. 24, 1975 [GB] United Kingdom ............... 43935/75

[51] Int. Cl.² ............................................. C07D 501/36
[52] U.S. Cl. ....................................... 424/246; 544/26
[58] Field of Search ........................................... 544/26

[56] References Cited

U.S. PATENT DOCUMENTS

| 3,953,439 | 4/1976 | Gleason | 544/26 |
| 3,989,694 | 11/1976 | Berges | 544/26 |
| 4,007,173 | 2/1977 | Hoover et al. | 544/26 |
| 4,039,536 | 8/1977 | Takano et al. | 544/26 |
| 4,080,451 | 3/1978 | Baxter et al. | 544/26 |

*Primary Examiner*—Nicholas S. Rizzo
*Attorney, Agent, or Firm*—Connolly and Hutz

[57] ABSTRACT

A series of novel 7-(D-α-aminophenylacetamido)- and 7-(D-α-hydroxyphenylacetamido)-Δ³-cephem derivatives have been prepared wherein a heterocyclic thiomethyl moiety is located at the 3-position of the molecule. These compounds are useful as antibacterial agents for the treatment of diseases caused by Gram-positive and Gram-negative bacteria. Preferred members include 7-(D-α-hydroxyphenylacetamido)-3-(3-carbamoyl-1,2,4-triazol-5-yl)thiomethylceph-3-em-4-carboxylic acid and 7-(D-α-hydroxyphenylacetamido)-3-(2-carboxymethoxy-methyl-1,3,4-thiadiazol-5-yl)thiomethylceph-3-em-4-carboxylic acid. Alternative methods of preparation are provided for these compounds, including various synthetic routes leading to the required novel heterocyclic thiol intermediates.

8 Claims, No Drawings

7-AMINOPHENYLACETAMIDO-Δ³-CEPHEM ANTIBACTERIAL AGENTS AND METHOD OF USE

CROSS REFERENCE TO RELATED APPLICATION

This application is a division of application Ser. No. 670,880 filed Mar. 26, 1976, now U.S. Pat. No. 4,080,451.

BACKGROUND OF THE INVENTION

This invention relates to new and useful antibacterial agents, and to their chemical methods of preparation. More specifically, it is concerned with a novel class of cephalosporin derivatives which possess broad spectrum antibacterial activity against both Gram-positive and Gram-negative microorganisms. In particular, the compounds of the invention constitute a series of 7-(α-aminophenylacetamido)- and 7-(α-hydroxyphenylacetamido)-Δ³-cephem derivatives with a thiomethyl moiety attached to the cepham nucleus at the 3-position of the molecule.

In the past, various attempts have been made by numerous investigators in the field of chemotherapy to obtain new and better antibacterial agents. For the most part, these efforts have involved the synthesis and testing of various new and heretofore unavailable organic compounds, particularly in the area of semisynthetic antibiotics like the cephalosporin derivatives. For instance J. S. G. Cox et al. in U.S. Pat. No. 3,278,531 and German Offenlegungsschrift No. 2,262,262 to Fujisawa both broadly disclose various 7-(D-acylamino)-3-(heterocyclic)thiomethylceph-3-em-4-carboxylic acid derivatives alleged to be useful for these purposes. However, in the search for still new and more improved antibacterial agents, little is know about the effect of certain particular novel heterocyclic thiomethyl moieties on compounds of this type, especially when the heterocyclic nucleus bears one of a series of certain speciified substituents.

SUMMARY OF THE INVENTION

According to the present invention, there are provided novel cephalosporin compounds of the general formula:

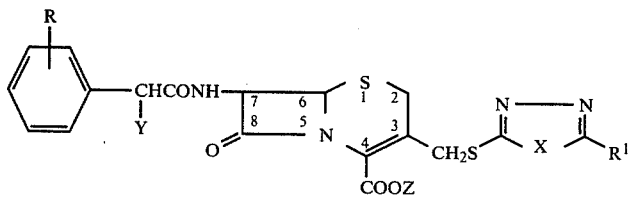

and the pharmaceutically acceptable salts thereof, wherein R is a member selected from the group consisting of hydrogen and hydroxyl; Y is a member selected from the group consisting of amino, hydroxyl and $OR^4$ wherein $R^4$ is chosen from the group consisting of lower alkanoyl, lower alkoxycarbonyl and benzoyl; Z is a member selected from the group consisting of hydrogen, lower alkyl, benzhydryl, phenyl, indan-5-yl, lower alkylcarbonyloxymethyl, lower α-(alkoxycarbonyloxy)ethyl and 3-phthalido; $R^1$ is a member selected from the group consisting of carboxymethyoxymethyl, lower alkoxycarbonylmethoxymethyl, $CH_2OCH_2CONR^2R^3$ wherein $R^2$ and $R^3$ are each chosen from the group consisting of hydrogen and lower alkyl, and $CONR^2R^3$ wherein $R^2$ and $R^3$ are each chosen from the group consisting of hydrogen and lower alkyl; and X is a member selected from the group consisting of oxygen, sulfur, imino and N-methylimino.

The pharmaceutically acceptable salts of the compounds of the invention include the pharmaceutically acceptable base salts derived from pharmacologically acceptable cations and they, in turn, include non-toxic metallic salts, particularly of lithium, sodium, potassium, calcium and aluminum, as well as ammonium and substituted ammonium salts, such as salts of trialkylamines, N-ethylpiperidine, procaine, dibenzylamine, N-benzyl-β-phenylethylamine, 1-ephenamine, N,N¹-dibenzylethylenediamine, dehydroabietylamine, N,N¹-bis-dehydroabietylethylenediamine and other amines previously used to form salts with benzylpenicillin. Compounds of the invention which are sufficiently basic in nature, e.g., those in which Y is an amino group, can also form acid addition salts and hence, the invention includes pharmaceutically acceptable acid addition salts within its scope. These particular salts are all derived from non-toxic acids having pharmacologically acceptable anions and they include the hydrochloride, hydrobromide, sulfate or bisulfate, phosphate or acid phosphate, acetate, maleate, furmarate, lactate, tartrate, citrate, gluconate, succinate, trifluoroacetate and p-toluenesulfonate salts. It should be additionally appreciated in this connection that compounds in which Y is amino may also exist in a zwitterionic form.

Throughout this specification, it is to be understood that by the use of the term "lower" before alkyl and alkoxy and alkanoyl, we mean those such groups which contain up to four carbon atoms. In the case of those alkyl and alkoxy groups which contain at least three carbon atoms and those alkanoyl groups which contain four carbon atoms, the carbon chain may either be straight or branched.

A preferred group of compounds of the present invention are those of the formula (I) in which R is hydrogen or p-hydroxyl, Y is amino or hydroxyl, Z is hydrogen, $R^1$ is a member selected from the group consisting of carboxymethoxymethyl, lower alkoxycarbonylmethoxymethyl, $CH_2OCH_2CONR^2R^3$ wherein $R^2$ and $R^3$ are each hydrogen, and $CONR^2R^3$ wherein $R^2$ and $R^3$ are also each hydrogen, and X is sulfur or imino. It should also be noted that when R is p-hydroxyl, Y is preferably amino. Typical member compounds of the preferred class include such compounds as 7-(D-α-hydroxyphenylacetamido)-3-(3-carbamoyl-1,2,4-triazol-5-yl)thiomethylceph-3-em-4-carboxylic acid, 7-(D-α-amino-p-hydroxyphenylacetamido)-3-(3-carboxymethoxymethyl-1,2,4-triazol-5-yl)thiomethylceph-3-em-4-carboxylic acid, 7-(D-α-amino-p-hydroxyphenylacetamido)-3-(3-carbamoylmethoxymethyl-1,2,4-triazol-5-yl)thiomethylceph-3-em-4-carboxylic acid, 7-(D-α-amino-p-hydroxyphenylacetamido)-3-(3- carbamoyl-1,2,4-triazol-5-yl)thiomethylceph-3-em-4-carboxylic acid, 7-(D-α-hydroxyphenylacetaido)-3-(3-carboxymethoxymethyl-1,2,4-triazol-5-yl)-thiomethyl-ceph-3-em-4-carboxylic acid, 7-(D-α-hydroxyphenylacetamido)-3-(2-ethoxycarbonylmethoxymethyl-1,3,4-thiadiazol-5-yl)thiomethylceph-3-em-4-carboxylic acid and 7-(D-α-hydroxyphenylacetamido)-3-(2-carboxymethoxymethyl-1,3,4-thiadiazol-5-yl)thiomethylceph-3-em-4-carboxylic acid, as well as 7-(D-α-hydroxyphenylacetamido)-3-(2-carboxymethoxymethyl-1,3,4-oxadiazol-5-yl)thiomethylceph-3-em-4-carboxylic acid.

It is to be understood that in the case of those compounds of the invention in which X is imino, tautomerisin is possible between the structure in which the hydrogen atom resides at the 4-position and the structures in which the hydrogen atom resides at either the 1- or 2-positions of the molecule, respectively.

The cephalosporin derivatives of the present invention are also capable of existing in epimeric D- and L-forms, and the invention includes the separated D- and L- epimers as well as racemic DL-mixtures thereof as all being well within its scope. However, the D-compounds of the present invention are more preferred for the present purposes at hand.

The invention also includes within its scope various novel pharmaceutical compositions comprising a compound of the formula (I) together with a pharmaceutically acceptable carrier or diluent, and it additionally provides a method for treating an animal of diseases caused by Gram-positive and Gram-negative bacteria by administering to said animal an antibacterially-effective amount of a compound of the formula (I) or a pharmaceutical composition thereof as hereinbefore defined.

Additionally, the invention also includes within its scope various novel heterocyclic thiol compounds which are useful as intermediates leading to the production of the aforementioned cephalosporin final products. These particular heterocyclic thiols all possess either a 1,3,4-thiazole, 1,3,4-oxadiazole or 1,2,4-triazole ring nucleus and even more specifically, are of the following general structural formula:

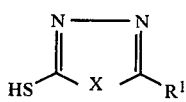
(VIII)

including the ammonium and alkali salts thereof, wherein $R^1$ is a member selected from the group consisting carboxymethoxymethyl, lower alkoxycarbonyl-methoxymethyl, $CH_2OCH_2CONR^2R^3$ wherein $R^2$ and $R^3$ are each chosen from the group consisting of hydrogen and lower alkyl, and $CONR^2R^3$ wherein $R^2$ and $R^3$ are each chosen from the group consisting of hydrogen and lower alkyl; and X is a member selected from the group consisting of oxygen, sulfur, imino, N-methylimino, benzylimino and p-methoxybenzylimino with the proviso that when X is amino, N-methylimino, N-benzylimino or N-methoxybenzylimino and $R^1$ is $CONR^2R^3$, $R^2$ and $R^3$ are not both lower alkyl, since such compounds have already been disclosed in British Patent No. 1206170 to Laboratoire Roger Bellon. It should be noted that when $R^1$ is carboxymethoxymethyl, the salts may also be dialkali and diammonium, etc.

A preferred group of heterocyclic thiols of the present invention are those of the formula (VIII) wherein $R^1$ is a member selected from the group consisting of carboxymethoxymethyl, lower alkoxycarbonylmethoxymethyl, $CH_2OCH_2CONR^2R^3$ wherein $R^2$ and $R^3$ are each hydrogen, and $CONR^2R^3$ wherein $R^2$ and $R^3$ are also each hydrogen, and X is oxygen, sulfur, imino or N-methylimino, including their sodium and potassium salts. Typical member compounds of the preferred class include such compounds as 3-carbamoyl-1,2,4-triazole-5-thiol, 3-(carboxymethoxymethyl)-1,2,4-triazole-5-thiol, 3-(carbamoylmethoxymethyl)-1,2,4-triazole-5-thiol, 2-(carboxymethoxymethyl)-1,3,4-thiadiazole-5-thiol and 2-(carboxymethoxymethyl)-1,3,4-oxadiazole-5-thiol.

It is to be understood that the heterocyclic thiol compounds of structural formula (VIII) may possibly exist in a tautomeric form, as will be readily appreciated by those skilled in the art.

DETAILED DESCRIPTION OF THE INVENTION

The compounds of the invention may be prepared in a number of ways, including the following:

(1) The compounds can be prepared by acylating a 7-amino-3-heterocyclicthiomethyl-$\Delta^3$-cephem derivative of the formula:

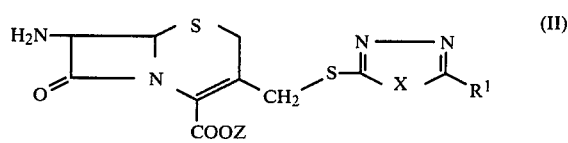
(II)

with an acylating agent of the formula:

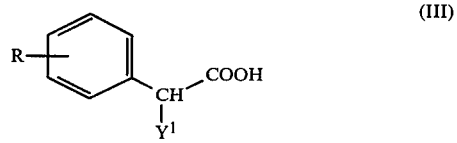
(III)

wherein $Y^1$ is a protected amine or a protected hydroxyl group or a group of the formula $-OR^4$, or with its functional equivalent as an acylating agent, for example, an acid chloride or bromide, or an "activated" ester or a mixed anhydride, followed by the removal of the protecting group in $Y^1$. The acylating agent employed (III) is preferably one that is in the D-form.

The acid chloride or bromide may be obtained by conventional methods. For example, the acid chloride may be obtained by reacting the acid (III) in a suitable solvent with oxalyl or thionyl chloride, or with phosgene.

The preferred "activated" ester has the formula:

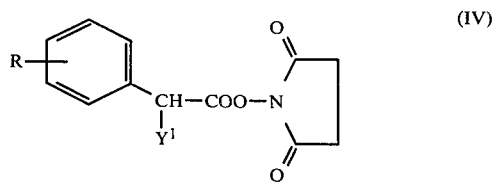
(IV)

and may be prepared by reacting the acid (III) with N-hydroxysuccinimide in the presence of a dehydrating agent, e.g., dicyclohexylcarbodiimide.

Suitable mixed anhydrides have the formula:

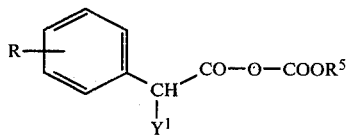

(V)

wherein $R^5$ is a lower alkyl group and most preferably, an iso-butyl group. The mixed anhydride is typically prepared by the reaction of a solution of the acid (III) in a suitable solvent, e.g., dry tetrahydrofuran, containing about one equivalent amount of a suitable base, e.g. triethylamine, with a lower alkyl chloroformate, e.g., iso-butyl chloroformate. The reaction should be carried out at a low temperature, e.g., $-10°$ C. to $0°$ C., and is generally completed within a few minutes.

It should be understood that the term "functional equivalent as an acylating agent" when applied to compound (III) also includes the "internally protected" dione of the formula:

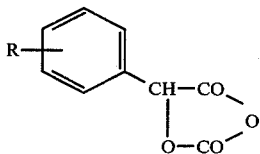

(VI)

The dione may be prepared by the reaction of phosgene with a suitably substituted phenylacetic acid.

Suitable protecting groups in $Y^1$ are those commonly employed in the art. The preferred protecting group for an amino group is a tertiary-butoxycarbonyl group, and, for an hydroxyl group, a formyl or dichloroacetyl group. In the preparation of the acid chlorides or bromides, HCl or HBr is evolved which will protonate any free -NH₂ groups represented by Y. The proton may act as a suitable "protecting group", and no introduction of a tert.-butoxycarbonyl group may then be necessary, with the solution containing the protonated acid chloride or bromide being coupled directly with the compound (II).

When the acylation is carried out by reacting the free acid (III) with the compound (II), it is generally necessary to protect any free carboxyl groups in (II) prior to reaction. The reaction should be carried out in the presence of a dehydrating agent, e.g., dicyclohexylcarbodiimide or 1-ethyl-3-(3-dimethylaminoprop-1-yl)carbodiimide hydrochloride. Protection of any free carboxyl group (e.g., by trimethylsilyl groups) is generally essential when using dicyclohexylcarbodiimide, but may not be necessary when using 1-ethyl-3-(3-dimethylaminoprop-1-yl)carbodiimide hydrochloride. In a typical reaction, compound (II) and a base, e.g., triethylamine, are dispersed in a suitable solvent, e.g., dry methylene chloride, followed by the addition of trimethylsilyl chloride when any free carboxyl groups are present in (II). After stirring for about an hour, a solution of compound (III) and a dehydrating agent, e.g., dicyclohexylcarbodiimide, in a suitable solvent, e.g., methylene chloride, is added and the resulting solution is stirred for several hours. After filtration, the organic filtrate may be shaken with an aqueous acid, e.g., hydrochloric acid, to remove any trimethylsilyl protecting groups, and, after separation, the organic phase is subsequently dried over anhydrous magnesium sulfate. Although the reaction can be carried out at room temperature, it is preferably carried out at a low temperature, e.g., $-5°$ C. to $0°$ C. The product obtained after evaporation of the reaction mixture to dryness will, of course, be a cephalosporin having a protected amino or a protected hydroxyl group. Such protecting groups may then be removed by conventional procedures. For example, a tert.-butoxycarbonyl group may be removed by means of acid hydrolysis, using, for example, formic acid or anhydrous trifluoroacetic acid at about $0°$ C. In the case of the latter acid, the desired product of formula (I) is conveniently obtained in the form of its trifluoroacetic acid addition salt after evaporation of the reaction mixture in vacuo and trituration of the resulting oil with dry diethyl ether. The trifluoroacetate salt may then be converted to its zwitterionic form, or to a pharmaceutically acceptable acid addition salt thereof, by methods conventional in the art. For example, when Z is a hydrogen atom, the zwitterionic form of the compound may be obtained by treating a suspension of the trifluoroacetate salt in water with aqueous caustic soda to adjust the pH of the resulting solution to about 7.5, followed by filtration and the subsequent addition of hydrochloric acid to reduce the pH to a value of about 3.5 so as to precipitate the zwitterionic product. Formyl and dichloroacetyl protecting groups may then be removed by means of aqueous base, e.g., aqueous sodium bicarbonate solution, which, when Z is a hydrogen atom, produces the sodium salt of the corresponding cephalosporin. The free acid may then be obtained by means of acidification. In a typical procedure, the hydroxyl-protected cephalosporin is dispersed in aqueous sodium bicarbonate solution, and the resulting solution is overlayered with a suitable water-immiscible organic solvent, e.g. ethyl acetate. After acidification of the aqueous phase to a pH value of about 2.0, the organic phase is then separated, dried and subsequently evaporated in vacuo to leave an oil which can then be triturated with dry diethyl ether to yield the free acid form of the desired α-hydroxy-cephalosporin.

In a typical procedure involving the reaction of a mixed anhydride (V) with the compound (II), the latter compound is first dissolved, if necessary, with the aid of a base such as triethylamine, in a suitable solvent, e.g., aqueous tetrahydrofuran, and then mixed with a solution of the anhydride in, for example, tetrahydrofuran. After mixing for a period of about an hour, preferably at a temperature of $-10°$ C., to $0°$ C., the coolant is then removed and the solution allowed to stand for several hours, followed by dilution with water and extraction with a suitable water-immiscible organic solvent, e.g. ethyl acetate, to remove all the impurities into the organic phase. After separation, the aqueous phase may be overlayered with a suitable water-immiscible organic solvent, e.g. ethyl acetate, and then acidified to about pH 2.0 by the addition of hydrochloric acid so as to induce extraction of the desired product into the organic phase. The separated organic phase may then be dried over anhydrous magnesium sulfate and evaporated in vacuo, with the resulting oil thereafter crystallized by means of trituration with dry diethyl ther. The product is, of course, the protected cephalosporin, and the protecting groups may then be removed as hereinbefore described. The reaction of the activated ester (IV) with the compound (II) can also be carried out in a similar manner.

In a typical reaction involving the acylation of the compound (II) with an acid chloride, the acid chloride is first dispersed in a suitable solvent, e.g., dry acetone, and then added to a solution of the compound (II) in, for example, aqueous acetone containing sodium bicarbonate. After mixing for about an hour at low temperature, e.g., 0° C., the coolant may then be removed and stirring thereafter continued for a period of several hours. Water and a water-immiscible solvent such as ethyl acetate are then added, and the pH of the aqueous phase is subsequently adjusted to about pH 2.0 with, for example, hydrochloric acid. After filtration, the organic phase may then be separated and the aqueous phase thereafter extracted with fresh ethyl acetate. The two organic phases are then combined, evaporated in vacuo and subsequently triturated with dry diethyl ether. The product is, once again, a cephalosporin having a protected amino or a protected hydroxyl group, and the protecting groups are then removed as described before. The acid bromide also reacts in a similar manner.

Acylation with the "internally protected" dione (VI) is also effected in a similar manner to the acid chloride procedure, with the products obtained being, of course, a cephalosporin in which Y is —OH.

The starting compound of the formula (II) wherein Z is hydrogen are readily obtained by employing methods analogous to those already described in the prior art. For example, 7-aminocephalosporanic acid is reacted with the appropriate heterocyclic thiol in an aqueous medium at 50°–70° C. for a period of 1–2 hours, employing a pH in the range of 6.5–7.5. Alternatively, 7-formamidocephalosporanic acid can be reacted with the appropriate heterocyclic thiol in a phosphate buffer at 50°–75° C., employing a pH in the range of 6.5–8.0, followed by subsequent removal of the formyl group via methanolic hydrogen chloride. In some instances, the latter route appears to afford the purer starting material insofar as compound (II) is concerned.

The compounds of the formula (II) in which Z is other than hydrogen, i.e., those compounds wherein Z completes an ester group, may also be prepared by methods analogous to those of the prior art, e.g., by esterifying the corresponding amino-protected compound (II) in which Z is hydrogen or an alkali metal atom like potassium via the use of such typical reagents as a $C_1$–$C_4$ diazoalkane (e.g., diazomethane), diphenyl diazomethane, phenol and indan-5-ol, with the latter two both being employed in conjunction with a dehydrating agent like dicyclohexylcarbodiimide. Alternatively, they may also be prepared by esterifying the corresponding amino-protected compound where Z is an alkali metal atom (preferably, potassium) via the use of such reagents as a chloromethyl lower alkanoate, an α-chloroethyl lower alkyl carbonate or 3-chlorophthalide (the corresponding bromo compounds may also be respectively used in this connection). Needless to say, in carrying out these esterification reactions, it may also be necessary to protect any free carboxyl groups in $R^1$ prior to the reaction, followed by the removal of the protecting groups thereafter in accordance with conventional procedure. Moreover, in the second type esterification reaction (involving a metathetical reaction), some isomerism of the double bond at the 2-position in the cephem nucleus may occur, but this can be reversed by forming the S-oxide derivative of the product and then reducing in a known manner.

(2) The compounds of the invention in which Y is OH or $NH_2$ and Z is hydrogen can also be prepared by reacting a cephalosporin derivative of the formula:

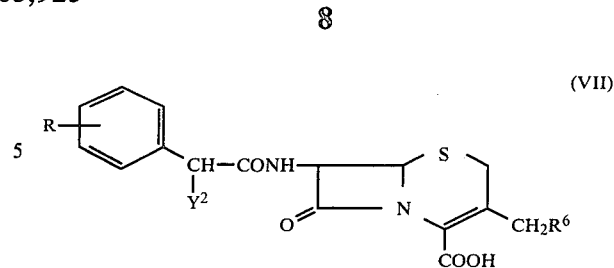

(VII)

wherein $Y^2$ is OH, $NH_2$ or a protected hydroxyl or a protected amino group and $R^6$ is a suitable "leaving" group, e.g., a chloro, bromo, iodo or, and most preferably, an acetoxy group, with a heterocyclic thiol compound of the formula:

(VIII)

or with a metal or ammonium salt thereof, followed by, if necessary, the removal of any protecting groups from $Y^2$. The compound (VII) is preferably in the D-form, while the metal salt of the thiol is preferably an alkali metal salt, and most preferably, a sodium or potassium salt, e.g., of the formula:

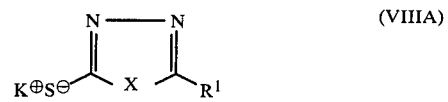

(VIIIA)

In the case where $R^1$ contains a —COOH group, the thiol may be reacted in the form of its di-metal salt, e.g.,

(VIIIB)

Needless to say, $Y^2$ is preferably a protected amino group, e.g., a tert.-butoxy-carbonylamino group, or a free hydroxyl group. Unprotected amino groups tend to react with the β-lactam system of the cephalosporin ring under the present reaction conditions. However, in most cases, there is no need to protect an α-hydroxyl group.

The reaction is typically carried out in a phosphate buffer solution at a pH of from about 6.5 to about 8.0 in order to ensure the existence of the required anion, viz.,

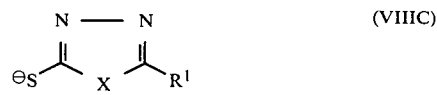

(VIIIC)

and at a temperature of from about 50° C. to about 75° C. After several hours, the reaction mixture may be cooled and overlayered with a suitable water-immiscible organic solvent, e.g., ethyl acetate, in order to extract the impurities into the organic phase. After separation, the aqueous phase is then overlayered with fresh ethyl acetate and subsequently treated with aqueous hydrochloric acid to reduce the pH to a low value, e.g., pH 2.0, so as to induce extraction of the product into the organic phase. The separated organic phase is then washed with saturated aqueous sodium chloride, dried over anhydrous magnesium sulfate and subsequently evaporated in vacuo. The resulting oil may then be crystallized by means of trituration with dry diethyl ether. Any amino- or hydroxy- protecting groups in the cephalosporin product are then removed as hereinbefore described in method (1).

The starting materials of the formula (VII) are either known compounds or else they may be prepared by methods analogous to those already described in the prior art. The other starting materials of the general formula (VIII), i.e., the heterocyclic thiols which are also used as the initial reagents in general procedure (1), are (with the proviso already mentioned) novel compounds and may be prepared by a number of routes, including the following:

(a) For instance, the thiadiazoles of the invention may be prepared by the acid-catalyzed cyclization of a compound of the formula:

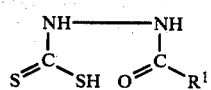
(IX)

or an alkali metal salt thereof, wherein $R^1$ is as previously defined for formula (I). In a typical procedure, the compound of the formula (IX) is added slowly to concentrated sulfuric acid at a low temperature, e.g., 0° C. After a short period of time, the reaction mixture is then carefully added to an ice-water mixture to precipitate the desired product therefrom. The latter can then be filtered off, washed with water and dried. Compounds of the formula (IX), on the other hand, are prepared by conventional methods, e.g., by reacting a compound of the formula $R^1CONHNH_2$ with carbon disulfide in the presence of base.

(b) The oxadiazoles of the formula (VIII) may be prepared by the base-catalyzed cyclization of a compound of the formula (IX) or an alkali metal salt thereof. In a typical reaction, the compound (IX) is reacted in a suitable solvent with potassium hydroxide dissolved in absolute alcohol.

(c) The compounds of the formula (VIII) in which X is NMe may be prepared by cyclizing a compound of the formula (XI), which may, in turn, be prepared by reacting a compound of the formula $R^1CONHNH_2$ (X) with methyl isothiocyanate.

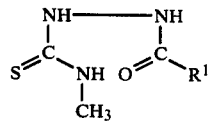
(XI)

In some cases, the compound (XI) may be cyclized to the desired product merely by heating, although the presence of a base such as sodium hydride is usually necessary. In a typical reaction, a solution of methyl isothiocyanate in a suitable solvent, e.g., dry tetrahydrofuran, is added slowly to a solution of the hydrazide (X) in a suitable solvent, e.g., absolute alcohol, and the reaction mixture is then stirred at room temperature (~25° C.) for several hours, filtered and the filtrate subsequently evaporated in vacuo and thereafter triturated with a solvent like dry diethyl ether to obtain the intermediate (IX). It is not, however, absolutely essential to isolate the intermediate. The intermediate can then be added to a solution of sodium hydride in a suitable solvent, e.g., dry ethanol, and the resulting reaction mixture thereafter heated, e.g., under reflux, for several hours, cooled and then acidified with, e.g., dilute hydrochloric acid, to a low pH value, e.g., pH 2.0. The organic solvent is then removed in vacuo, the aqueous residue extracted with a suitable solvent, e.g., ethyl acetate, and the organic phase dried and subsequently evaporated to dryness in order to obtain the desired product.

(d) The compounds of the formula (VIII) in which X is NH may be prepared by employing procedures similar to those hereinbefore described in (c), but using isothiocyanic acid in place of methyl isothiocyanate. Preferably, however, the compounds in which X is NH are prepared by cyclizing a compound of the formula:

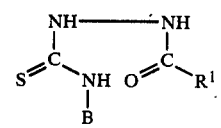
(XII)

wherein B is a benzyl group or p-methoxybenzyl group, to produce a compound of the formula:

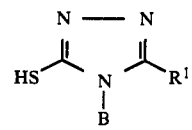
(XIII)

and then removing the group B. In general, the compoud (XII) cyclizes on heating, although the presence of a base such as sodium hydroxide may sometimes be necessary. The group B, when necessary, can be removed by reaction with trifluoroacetic acid (or other suitable strong acid) or by reduction with hydrogen. The compounds of the formula (XII) may be prepared by reacting a compounds of the formula $R^1CONHNH_2$ (X) with benzyl- or p-methoxy-benzyl-isothiocyanate.

Thus, in a typical reaction, the isothiocyanate and the compound (X) are heated, e.g., under reflux in a suitable solvent, e.g., absolute alcohol, for several hours. The reaction mixture is then filtered and the filtrate subsequently evaporated in vacuo, with the resulting oil being triturated with, e.g., dry diethyl ether to obtain the intermediate of the formula (XIII). The intermediate is then preferably de-protected by a suitable strong acid, e.g., trifluoroacetic acid, and this is typically carried out by heating the intermediate in a mixture of trifluoroacetic acid and anisole for a few hours, followed by cooling, evaporating the reaction mixture in vacuo and then triturating the resulting product with a suitable solvent.

(e) The compounds of the formula (VIII) in which $R^1$ is a $-CH_2OCH_2CONR^2R^3$ or $-CONR^2R^3$ group may be prepared from the corresponding compounds in which $R^1$ is a $-CH_2OCH_2COO(C_1-C_4$ alkyl$)$ or $-COO(C_1-C_4$ alkyl$)$ group, respectively, by reaction with a compound of the formula $R^2R^3NH$. When ammonia is used, it is preferably employed in the form of ammonia-saturated ethanol. The compounds in which $R^1$ is a $-COO(C_1-C_4$ alkyl$)$ group may be prepared by methods (a) to (d) hereinbefore described, but utilizing as starting materials compounds in which $R^1$ is a $-COO(C_1-C_4$ alkyl$)$ group. The compounds in which $R^1$ is a —$CH_2OCH_2COOH$ group may be prepared from their corresponding $C_1$–$C_4$ alkyl esters by means of acid or alkaline hydrolysis. The esters may also be obtained from the corresponding acids by means of esterification, e.g., with a $C_1$–$C_4$ alkanol. All the foregoing reactions in this section may be carried out either before or after removal of the group B.

(f) The salts of the compounds of the formula (VII) may be prepared by conventional methods, e.g., by reacting the thiol with an aqueous or ethanolic solution of the appropriate alkali metal hydroxide.

(3) As regards the compounds of the formula (I) in which Z is other than hydrogen, these may alternately (and preferably) be prepared by esterification of the corresponding compounds of the formula (I) in which Z is hydrogen or an alkali metal atom (preferably potassium), with any free hydroxyl or amino groups represented by Y and any free carboxyl groups in $R^1$ being, if necessary, protected prior to the esterification reaction and then de-protected afterwards. The esterification step per se may, for example, be carried out by using the reagents earlier described in greater detail in general procedure (1).

(4) Salts of the compounds of the invention can be prepared, if desired, by standard techniques. For example, preparation of a sodium or potassium salt may be accomplished by dissolving a compound in which Z is hydrogen in a suitable organic solvent such as a lower alkanol and then adding a solution of the appropriate alkali metal acetate in the same solvent to the stirred organic solution. After reaction, the salt is typically isolated by concentration of the reaction mixture via partial evaporation in vacuo and then adding the concentrate to a large volume of a suitable organic solvent, e.g., diethyl ether, thereby precipitating the salt. Acid addition salts of those compounds of the invention in which Y is an amino group may be prepared by dispersing the cephalosporin derivative in water and then acidifying to a low pH value (e.g., pH 2.0) by the use of an appropriate acid, e.g., hydrochloric acid. The salt product is then recovered from the aqueous solution by evaporating the latter to dryness, preferably by freeze-drying.

The activity of the compounds of the present invention as antibacterials is clearly ascertained by their in vitro evaluation. The latter step was carried out by first determining the minimum inhibitory concentration (M.I.C.) of the individual test compound in a suitable nutrient medium containing the desired microorganism. The minimum inhibitory concentration (M.I.C.) is the level at which growth of the particular microorganism failed to occur. In practice, agar (i.e., brain/heart infusion agar) plates, each having incorporated therein the test compound at a particular concentration, were inoculated with a standard number of cells of the test microorganism and each plate was thereafter incubated for 24 hours at 37° C. The plates were then observed for the presence or absence of the growth of bacteria and the appropriate M.I.C. value noted. Microorganisms used in such tests and against which the compounds of the present invention were active included strains of *Escherichia coli, Klebsiella pneumoniae, Aerobacter aerogenes, Serratia marcescens, Proteus mirabilis, Proteus vulgaris, Staphylococcus aureus* and *Streptococcus pyogenes.*

A selection of M.I.C. values for many of the compounds of the invention, as hereinafter exemplified, with respect to their activities against certain of the various strains of microorganisms mentioned above is given below in the following table for illustrative purposes:

| Example No. of Compound | Escherichia coli 51A266 | Klebsiella pneumoniae 53A009 | Aerobacter aerogenes 55A004 | Serratia marcescens 63A001 | Proteus mirabilis 57C015 | Proteus vulgaris 57C060 | Staphylococcus aureus 01A005 | Strephtococcus pyogenes 02C203 |
|---|---|---|---|---|---|---|---|---|
| XXI | 1.56 | 3.12 | 3.12 | 100 | 3.12 | 3.12 | 12.5 | 1.56 |
| XXII | 6.25 | 6.25 | 12.5 | 100 | 12.5 | 12.5 | 6.25 | 0.78 |
| XXIII | 12.5 | 3.12 | 3.12 | 100 | 3.12 | 6.25 | 25 | 3.12 |
| XXIV | 1.56 | 0.78 | 1.56 | 100 | 1.56 | 1.56 | 0.39 | 0.39 |
| XXV | 1.56 | 0.39 | 0.39 | 100 | 0.39 | 0.39 | 1.56 | 0.39 |
| XXVI | 1.56 | 0.78 | 1.56 | 100 | 12.5 | 6.25 | 0.39 | 0.19 |
| XXVII | 1.56 | 0.78 | 1.56 | 100 | 1.56 | 1.56 | 0.39 | 0.09 |
| XXVIII | 0.78 | 0.78 | 0.78 | 100 | 1.56 | 3.12 | 3.12 | 0.78 |
| XXIX | 1.56 | 0.78 | 0.78 | 100 | 0.78 | 0.78 | 3.12 | 0.39 |
| XXX | 50 | 25 | 12.5 | 100 | 100 | 25 | 12.5 | 0.39 |
| XXXI | 3.1 | 6.2 | 6.2 | 100 | 12.5 | 12.5 | 1.56 | 0.098 |
| XXXII | 0.39 | 0.19 | 0.39 | 100 | 0.78 | 0.78 | 0.78 | 0.012 |
| XXXIV | 6.2 | 6.2 | 6.2 | 100 | 12.5 | 12.5 | 6.2 | 0.098 |
| XXXV | 6.2 | 12.5 | 6.2 | — | 50 | 50 | 6.2 | 0.19 |
| XXXVI | 50 | 50 | 25 | 100 | 100 | 100 | 50 | 0.78 |
| XXXVII | 50 | 50 | 50 | 50 | 50 | 50 | 25 | 0.78 |
| XXXVIII | 100 | 100 | 100 | 100 | 100 | 50 | 0.78 | |
| XXXIX | 50 | 50 | 50 | 100 | 100 | 100 | 100 | 0.78 |
| XL | 100 | 100 | 100 | 100 | 100 | 100 | 50 | 0.78 |
| XLI | 100 | 100 | 100 | 100 | 100 | 100 | 50 | 0.39 |
| XLII | 25 | 25 | 25 | 100 | 25 | 25 | 25 | 0.39 |
| XLIII | 100 | 100 | 100 | 100 | — | 100 | 6.2 | 0.19 |
| XLIV | 12.5 | 6.2 | 12.5 | 100 | 25 | 25 | 6.2 | 0.19 |
| XLV | 6.2 | 6.2 | 6.2 | 100 | 25 | 25 | 6.2 | 0.098 |
| XLVI | 25 | 6.2 | 6.2 | 100 | 12.5 | 12.5 | 25 | 0.39 |
| XLVII | 6.2 | 1.6 | 3.1 | 100 | 3.12 | 3.12 | 50 | 1.6 |
| XLVIII | 12.5 | 3.12 | 3.12 | 100 | 6.2 | 3.12 | 12.5 | 1.56 |

The compounds of the invention can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavoring or coloring agents.

They may also be injected parenterally, i.e., intravenously, intramuscularly or subcutaneously. For parenteral administration, they are best used in the form of a sterile aqueous solution which may contain other solutes, e.g., sufficient saline or glucose to make the solution isotonic.

The compounds of the invention can be administered to human subjects either orally or parenterally for the treatment of diseases caused by Gram-positive and Gram-negative bacteria. In general, the dosage level will be in the range of approximately 125 mg. to 1.0 g. of active compound per day, taken in 2 to 4 divided daily doses, when given to the average adult human patient (70 kg.) for the present purposes at hand. However, variations will necessarily occur depending upon the weight and condition of the subject being treated and the particular route of administration chosen.

EXAMPLE I

Part A

Potassium 3-(Ethoxycarbonylmethoxyacetyl)dithiocarbazate

Ethoxycarbonylmethoxyacetohydrazide (15.0 g.) was suspended in chilled ethanol (200 ml.) at 0° C. and carbon disulfide (26.7 ml.) was next added dropwise to the suspension. A solution of potassium hydroxide (5.6 g.) in ethanol (60 ml.) was then added to the mixture over a period of 30 minutes, and the resulting reaction mixture was stirred at 0° C. for a further 30 minutes. Finally, the coolant was removed and the reaction mixture was stirred overnight for approximately 16 hours. The product, viz., potassium 3-(ethoxycarbonylmethoxyacetyl)dithiocarbazate, was subsequently removed from the mixture by means of filtration, washed successively with ethanol and diethyl ether and finally dried in vacuo to constant weight (yield, 43.5 g.). This product was immediately used in the next reaction step without any further purification being necessary.

Part B 2-(Ethoxycarbonylmethoxymethyl)-1,3,4-thiadiazole-5-thiol

The product of Part A (4.0 g.) was added portionwise, with stirring, over a period of 15 minutes to ice-cooled concentrated sulfuric acid (20 ml.). After the final addition was complete, the reaction mixture was stirred for a further ten minutes and then carefully added to an ice-water mixture (200 g.). The insoluble product, 2-(ethoxycarbonylmethoxymethyl)-1,3,4-thiadiazole-5-thiol, was removed by filtration, washed with water and finally dried in vacuo to constant weight (yield, 2.4 g.). The analytical sample was obtained as white needles melting at 80°–82° C. after recrystallization from 20% ethanol-water.

Analysis: Found: C, 35.83; H, 4.25; N, 11.85%. Calcd. for $C_7H_{10}N_2O_3S_2$: C, 35.90; H, 4.30; N, 11.96%.

EXAMPLE II

Di-Potassium Salt of 2-(Carboxymethoxymethyl)-1,3,4-thiazole-5-thiol

The product of Example I, Part B (6.0 g.) was added to a stirred solution of potassium hydroxide (4.5 g.) in absolute alcohol (150 ml.) and, after a period of one hour, the insoluble product was filtered off, washed successively with ethanol and diethyl ether, and finally dried in vacuo to constant weight. The yield of pale yellow solid was 7.0 g., and this proved to be the monohydrate of the di-potassium salt of 2-(carboxymethoxymethyl)-1,3,4-thiadiazole-5-thiol, m.p. 269°–270° C. (decomp.).

Analysis: Found: C, 20.5; H, 1.92; N, 9.19%. Calcd. for $C_5H_4N_2O_3S_2K_2.H_2O$: C, 20.00; H, 2.00; N, 9.33%.

EXAMPLE III 2-(Carbamoylmethoxymethyl)-1,3,4-thiadiazole-5-thiol

This product (m.p. 216°–217° C.) was prepared from the product of Example I by treating the latter with ammonia-saturated ethanol in a manner similar to that described in the procedure of Example XVI, Part C as hereinafter set forth.

Analysis: Found: C, 29.13; H, 3.48; N, 19.51%. Calcd. for $C_5H_7N_3O_2S_2$: C, 29.23; H, 3.44; N, 20.46%.

EXAMPLE IV 2-(N-Methylcarbamoyl)-1,3,4-thiadiazole-5-thiol

This product was prepared from the corresponding 2-ethoxycarbonyl compound by treatment with methylamine in a conventional manner. The starting 2-ethoxycarbonyl compound was obtained by the procedure of Example I, using the ethyl ester of oxalic acid monohydrazide and carbon disulfide as the starting materials for the present purposes at hand.

EXAMPLE V 2-(Ethoxycarbonylmethoxymethyl)-1,3,4-oxadiazole-5-thiol

A solution of potassium hydroxide (0.22 g.) in ethanol (2.5 ml.) was added to a suspension of ethoxycarbonylmethoxyacetohydrazide in ethanol (4 ml.), followed by the addition of carbon disulfide (0.95 ml.) and dimethyl sulfoxide (0.54 ml.), respectively. The reaction mixture was then refluxed for a period of 12 hours, cooled and filtered, and the resulting filtrate subsequently evaporated in vacuo. The residual oil so obtained was then dissolved in water, filtered and the filtrate acidifed to pH 2.0 with aqueous 2N hydrochloric acid. Extraction of the latter solution with ethyl acetate and subsequent evaporation of the solvent then yielded the desired product, viz., 2-(ethoxycarbonylmethoxymethyl)-1,3,4-oxadiazole-5-thiol, as a white solid material (yield, 0.5 g.), m.p. 101°–103° C.

Analysis: Found: C, 38.82; H, 4.45; N, 12.86%. Calcd. for $C_7H_{10}N_2O_4S$: C, 38.53; H, 4.62; N, 12.84%.

EXAMPLE VI

Di-Potassium salt of 2-(Carboxymethoxymethyl)-1,3,4-oxadiazole-5-thiol

The product of Example V (2.0 g.) was stirred at room temperature (~25° C.) in aqueous 2 N potassium hydroxide (20 ml.) for a period of four hours. The resulting solution was then overlayered with ethyl acetate and aqueous 2 N hydrochloric acid was subsequently added to reduce the pH to 2.0. The organic layer was next separated, dried over anhydrous magnesium sulfate and finally evaporated to yield a solid which was shown by thin chromatography to contain some unreacted starting material. The solid product (1.0 g.) was then stirred overnight (~16 hrs.) with a solution of ethanol (10 ml.) containing potassium hydroxide (0.5 g.) and the resulting insoluble solid, viz., the di-potassium salt of 2-(carboxymethoxymethyl)-1,3,4-oxadiazole-5-thiol, was filtered off, washed with ethanol and dried in vacuo to yield 1.0 g. of pure material melting at 207°–210° C. (decomp.)

EXAMPLE VII 2-(Carboxymethoxymethyl)-1,3,4-oxadiazole-5-thiol

A sample of the product of Example V was converted to the free acid by treatment with dilute hydrochloric acid in the usual manner. In this way, there was obtained pure 2-(carboxymethoxymethyl)-1,3,4-oxadiazole-5-thiol, m.p. 126°–129° C.

Analysis: Found: C, 31.69; H, 3.15; N, 14.63%. Calcd. for $C_5H_6N_2O_4S$: C, 31.58; H, 3.16; N, 14.74%.

EXAMPLE VIII

2-Carbamoyl-1,3,4-oxadiazole-5-thiol

This product was prepared by reacting 2-ethoxycarbonyl-1,3,4-oxadiazole-5-thiol with ammonia in a manner similar to that described in the procedure of Example XVI, Part C as hereinafter set forth. The 2-ethoxycarbonyl starting material was prepared by the procedure of Example V, except that the ethyl ester of oxalic acid monohydrazide was the reagent employed. In this way, there was ultimately obtained pure 2-carbamoyl-1,3,4-oxadiazole-5-thiol, m.p. 237° C. (decomp).

Analysis: Found: C, 24.92; H, 2.09; N, 28.53%. Calcd. for $C_3H_3N_3O_2S$: C, 24.82; H, 2.08; N, 29.95%.

EXAMPLE IX 2-(N-Methylcarbamoyl)-1,3,4-oxadiazole-5-thiol

This product was prepared by reacting 2-ethoxycarbonyl-1,3,4-oxadiazole-5-thiol with methylamine in a manner similar to that described in the procedure of Example XVI, Part C as hereinafter set forth.

EXAMPLE X 2-(N-Ethylcarbamoyl)-1,3,4-oxadiazle-5-thiol

This product (m.p. 210° C. with decomp.) was prepared by reacting 2-ethoxycarbonyl-1,3,4-oxadiazole-5-thiol with ethylamine in a manner similar to that described in the procedure of Example XVI, Part C as hereinafter set forth.

Analysis: Found: C, 35.00; H, 4.14; N, 24.00%. Calcd. for $C_5H_7N_3O_2S$: C, 34.67; H, 4.08; N, 24.26%.

EXAMPLE XI 2-(N,N-Dimethylcarbamoyl)-1,3,4-oxadiazole-5-thiol

This product (m.p. 185°–187° C.) was prepared by reacting 2-ethoxycarbonyl-1,3,4-oxadiazole-5-thiol with dimethylamine in a manner similar to that described in the procedure of Example XVI, Part C as hereinafter set forth.

Analysis: Found: C, 34.81; H, 3.99 N, 23.76%. Calcd. for $C_6H_9N_3O_2S$: C, 34.67; H, 4.08; N, 24.26%.

EXAMPLE XII

Part A 1-(Ethoxycarbonylmethoxyaceto)-4-methyl-3-thiosemicarbazide

A solution of methyl isothiocyanate (3.52 g.) in dry tetrahydrofuran (20 ml.) was added during the course of 30 minutes to a suspension of ethoxycarbonylmethoxyacetohydrazide (8.50 g.) in absolute alcohol (50 ml.), and the resulting mixture was stirred for a further period of two hours. The solution was then filtered and the clear filtrate evaporated in vacuo. Trituration of the residue with dry diethyl ether then gave the compound $CH_3NHCSNHNHCOCH_2OCH_2COOEt$ as a white solid material (yield, 8.0 g.).

Analysis: Found: C, 38.77; H, 6.21; N, 17.03%. Calcd. for $C_8H_{15}N_3O_4S$: C, 38.55; H, 6.02; N, 16.87%.

Part B 3-(Ethoxycarbonylmethoxymethyl)-4-methyl-1,2,4-triazole-5-thiol

The product of Part A (2.49 g.) was added to a solution of sodium hydride (0.3 g.) in dry ethanol (50 ml.) and the reaction mixture was refluxed for a period of four hours. The resulting mixture was then cooled and divided equally into two portions (i) and (ii). Aqueous 2 N hydrochloric acid was added to portion (i) to reduce the pH to 2.0, and the organic solvent present was then removed in vacuo. Extraction of the aqueous residue with ethyl acetate and subsequent evaporation of the desired organic layer (dried over anhydrous magnesium sulfate) then gave 3-(ethoxycarbonylmethoxymethyl)-4-methyl-1,2,4-triazole-5-thiol as a white solid, m.p. 86°–88° C. (yield, 300 mg.). The product was characterized by nuclear magnetic resonance and infrared absorption spectroscopy.

EXAMPLE XIII 3-(Carboxymethoxymethyl)-4-methyl-1,2,4-triazole-5-thiol

Portion (ii) from Example XII was evaporated in vacuo, and the residue subsequently dissolved in water, acidified with aqueous 2 N hydrochloric acid and then extracted with ethyl acetate. The dried organic extract (dried over anhydrous magnesium sulfate) was evaporated in vacuo to yield a white solid that was subsequently shown by thin layer chromatographic analysis to be a 50:50 mixture of the ester of Example XII and the desired acid. This mixture was then stirred in aqueous 2 N sodium hydroxide for a period of two hours, acidified with 2 N hydrochloric acid and extracted again with ethyl acetate. The dried organic extract (dried over anhydrous magnesium sulfate) was evaporated in vacuo to yield pure 3-(carboxymethoxymethyl)-4-methyl-1,2,4-triazole-5-thiol as a white solid (yield, 0.25 g.), m.p. 155°–156° C.

Analysis: Found: C, 35.68; H, 4.48; N, 20.73%. Calcd. for $C_6H_9N_3O_3S$: C, 35.46; H, 4.43; N, 20.69%.

EXAMPLE XIV 3-(Carbamoylmethoxylmethyl)-4-methyl-1,2,4-triazole-5-thiol

This product (m.p. 152°–153° C.) was prepared by reacting 2-(ethoxycarbonylmethoxymethyl)-4-methyl-1,2,4-triazole-5-thiol (the product of Example XII) with ethanolic ammonia in a manner similar to that described in the procedure of Example XVI, Part C as hereinafter set forth. The product was characterized by nuclear magnetic resonance spectroscopy.

EXAMPLE XV

3-Carbamoyl-4-methyl-1,2,4-triazole-5-thiol

This product was prepared by reacting 2-ethoxycarbonyl-4-methyl-1,2,4-triazole-5-thiol with ethanolic ammonia in a manner similar to that described in the procedure of Example XVI, Part C as hereinafter set forth. The 2-ethoxycarbonyl starting material was prepared by the procedure of Example XII, except that the ethyl ester of oxalic acid monohydrazide was the reagent employed. In this way, there was ultimately obtained pure 3-carbamoyl-4-methyl-1,2,4-triazole-5-thiol, m.p. 273°–275° C. (decomp.).

Analysis: Found: C, 30.28; H, 3.82; N, 35.44; S, 20.20% Calcd. for $C_4H_6N_4OS$: C, 30.28; H, 3.81; N, 36.20; S, 19.72%.

EXAMPLE XVI

Part A

3-Ethoxycarbonyl-4-(p-methoxybenzyl)-1,2,4-triazole-5-thiol

A solution of p-methoxybenzyl isothiocyanate (8.95 g.) and the ethyl ester of oxalic acid monohydrazide (6.8 g.) in ethanol (50 ml.) was refluxed for a period of approximately 16 hours (overnight). The hot solution was then filtered, the filtrate evaporated in vacuo and the resulting oil triturated with dry diethyl ester. The solid product so obtained, viz., 3-ethoxycarbonyl-4-(p-methoxybenzyl)-1,2,4-triazole-5-thiol (yield, 7.2 g.) was then recrystallized from ethanol-water to yield 4.0 g. of pure material. The analytical sample melted at 142°–144° C. after a further recrystallization from ethyl acetate/petroleum ether (b.p. 60°–80° C.).

Analysis: Found: C, 53.29; H, 5.12; N, 14.70% Calcd. for $C_{13}H_{15}N_3O_3S$: C, 53.25; H, 5.16; N, 14.33%.

Part B

3-Ethoxycarbonyl-1,2,4-triazole-5-thiol

A mixture of the product of Part A (4.8 g.) in 4:1 vol./vol. trifluoracetic acid/anisole (20 ml.) was heated at 60° C. for a period of four hours. The resulting solution was cooled, subsequently evaporated in vacuo and the residue triturated with petroleum ether (b.p. 60°–80° C.) to give an orange solid. The orange solid was then triturated with dry diethyl ether to yield 3-ethoxycarbonyl-1,2,4-triazole-5-thiol as a white solid product (yield, 1.9 g.), m.p. 192°–193° C. (decomp.).

Analysis: Found: C, 34.60; H, 4.07; N, 24.07%. Calcd. for $C_5H_7N_3O_2S$: C, 34.69; H, 4.08; N, 24.28%.

Part C

3-Carbamoyl-1,2,4-triazole-5-thiol

The product of Part B (14.5 g.) was heated at 100° C. overnight (~16 hrs.) in a bomb with saturated ethanolic ammonia (200 ml.). The reaction mixture was then evaporated in vacuo to yield 12.0 g. of the ammonium salt of 3-carbamoyl-1,2,4-triazole-5-thiol. Conversion of the latter product to an analytical sample of the free thiol was then effected by means acidification of an aqueous solution of the ammonium salt, with the free thiol precipitating as an off-white solid, m.p. 276° C. (decomp.). The product was characterized by infrared absorption spectroscopy.

Analysis: Found: C, 25.97; H, 3.00; N, 37.75%. Calcd. for $C_3H_4N_4OS$: C, 25.01; H, 2.80; N, 38.89%.

EXAMPLE XVII 3-(Carboxymethyl)-1,2,4-triazole-5-thiol

By employing a procedure similar to that described in Example XVI, Part A, 3-(ethoxycarbonylmethoxymethyl)-4-(p-methoxybenzyl)-1,2,4-triazole-5-thiol was prepared from ethoxycarbonylmethoxyacetohydrazide. The ethoxycarbonyl group was then hydrolyzed to the free acid using aqueous 2 N sodium hydroxide, and the p-methoxybenzyl blocking group was thereafter removed by using trifluoroacetic acid in a manner similar to that earlier described in Example XVI, Part B to finally give pure 3-(carboxymethoxymethyl)-1,2,4-triazole-5-thiol, m.p. 180°–182° C.

Analysis: Found: C, 32.13; H, 3.73; N, 22.47%. Calcd. for $C_5H_2N_3O_3S$: C, 31.75; H, 3.73; N, 22.22%.

EXAMPLE XVIII 3-(Carbamoylmethoxymethyl)-1,2,4-triazole-5-thiol

This product was prepared from 3-(ethoxycarbonylmethoxymethyl)-4-(p-methoxybenzyl)-1,2,4-triazole-5-thiol by reaction with ethanolic ammonia in a manner similar to that of Example XVI, Part C, followed by removal of the p-methoxybenzyl group with trifluoroacetic acid in a manner similar to that of Example XVI, Part B. The final product was characterized by nuclear magnetic resonance spectroscopy.

EXAMPLE XIX 3-(N-Ethylcarbamoylmethoxymethyl)-1,2,4-triazole-5-thiol

This product was prepared by a procedure similar to that of Example XVIII, except for the fact that ethylamine was the reagent employed in lieu of ethanolic ammonia. The final product was characterized by nuclear magnetic resonance spectroscopy.

EXAMPLE XX

Part A

1-Oxamoyl-4-(p-methoxybenzyl)-3-thiosemicarbazide

Sodium methoxide (5.4 g., 0.1 mole) and 4-(p-methoxybenzyl)-thiosemicarbazide (2.1 g., 0.1 mole) were stirred in methanol (200 ml.) for a period of five minutes. Ethyl oxamate (11.7 g., 0.1 mole) was then added to the mixture and the resulting mixture was refluxed for a period of three hours. At this point, most of the solvent was evaporated under reduced pressure, water (200 ml.) was added to the residue and the pH adjusted to 2.0 with dilute hydrochloric acid. The resulting solid was then filtered and subsequently dried in vacuo at 50° C. to yield pure 1-oxamoyl-4-(p-methoxybenzyl)-3-thiosemicarbazide (25.7 g., 91% yield), m.p. 185°–190° C.

Analysis: Found: C, 46.3; H, 4.87; N, 18.83%. Calcd. for $C_{11}H_{14}N_4O_3S$: C, 46.8; H, 5.00; N, 19.15%.

Part B

3-Carbamoyl-4-(p-methoxybenzyl)-1,2,4-triazole-5-thiol

Sodium hydroxide (0.4 g., 0.01 mole) and 1-oxamoyl-4-(p-methoxybenzyl)-3-thiosemicarbazide (2.82 g., 0.01 mole) were heated in water (20 ml.) on a steam bath for a period of two hours. The clear solution was then cooled and acidified with dilute hydrochloric acid. The resulting solid was filtered and subsequently dried in vacuo at 50° C. to afford 3-carbamoyl-4-(p-methoxybenzyl)-1,2,4-triazole-5-thiol (2.5 g., 94% yield), m.p. 240°–242° C. The analytical sample melted at 243°–245° C. after being crystallized from a mixture of dimethylformamide and diethyl ether.

Analysis: Found: C, 49.0; H, 4.51; N, 20.5%. Calcd. for $C_{11}H_{12}N_4O_2S$: C, 49.9; H, 4.58; N, 21.2%.

Part C

3-Carbamoyl-1,2,4-triazole-5-thiol

3-Carbamoyl-4-(p-methoxybenzyl)-1,2,4-triazole-5-thiol (2.0 g., 0.007 mole), trifluoroacetic acid (8 ml.) and anisole (2 ml.) were heated at 70° C. for 3.5 hours. At this point, most of the trifluoroacetic acid present was removed by means of evaporation under reduced pressure and the residue was subsequently triturated with diethyl ether. The resulting solid was then filtered, washed with diethyl ether and subsequently dried in vacuo at 50° C. to give pure 3-carbamoyl-1,2,4-triazole-5-thiol (1.0 g., 91% yield), m.p. 276°–278° C. The infrared absorption spectrum was identical to that of a reference sample prepared as described in Example XVI, Part C.

EXAMPLE XXI

Part A 7-(D-α-tert-Butoxycarbonylamino-p-hydroxyphenylacetamido)-3-3-carboxymethoxymethyl-1,2,4-triazol-5-yl)thiomethylceph-3-em-4-carboxylic Acid A solution of 3-acetoxymethyl-7-(D-α-tert-butoxycarbonylamino-p-hydroxyphenylacetamido)ceph-3-em-4-carboxylic acid (4.25 g.) and 3-carboxymethoxymethyl-1,2,4-triazole-5-thiol (1.53 g.) in pH 7.0 phosphate buffer (100 ml.) was adjusted to pH 7.2 by the addition of aqueous 2 N sodium hydroxide, and the resulting mixture was then heated at 70° C. for a period of three hours. The spent reaction mixture was then cooled to room temperature (~25° C.), extracted once with ethyl acetate and the resulting organic layer discarded. The aqueous layer was then overlayered with fresh ethyl acetate and the pH was subsequently adjusted to pH 2.5 by the addition of aqueous 2 N hydrochloric acid. The organic phase was then separated, washed with saturated aqueous sodium chloride, separated again and finally dried over anhydrous sodium sulfate. Evaporation of the dried extract and subsequent trituration of the resulting residue with dry diethyl ether then gave pure 7-(D-α-tert-butoxycarbonylamino-p-hydroxyphenylacetamido)-3-(3-carboxymethoxymethyl-1,2,4-triazol-5-yl)thiomethylceph-3-em-4-carboxylic acid (yield, 1.6 g.) as a white solid.

Part B 7-(D-α-Amino-p-hydroxyphenylacetamido)-3-(3-carboxymethoxymethyl-1,2,4-triazol-5-yl)thiomethylceph-3-em-4-carboxylic Acids as the Trifluoracetate Salt The product of Example XXI (1.5 g.) was stirred in ice-cold trifluoroacetic acid (12 ml.) for a period of ten minutes. The resulting solution was then added to dry diethyl ether (200 ml.), and the off-white precipitate thus obtained was quickly removed by means of filtration and subsequently dried in vacuo. The salt product was next purified by trituration with 50 ml. of 5:1 vol.-/vol. ethyl acetate/ethanol for a period of one hour. The total yield of dried material, viz., the trifluoroacetic acid salt of 7-(D-α-amino-p-hydroxyphenylacetamido)-3-(3-carboxymethoxymethyl-1,2,4-triazol-5-yl)thiomethylceph-3-em-4-carboxylic acid, was 1.1 g. The final product was characterized by both infrared absorption spectroscopy and nuclear magnetic resonance data.

EXAMPLE XXII 7-(D-α-Amino-p-hydroxyphenylacetamido)-3-(3-carbamoyl-1,2,4-triazol-5-yl)thiomethylceph-3-em-4-carboxylic Acid as the Trifluoroacetate Salt This product was prepared by employing procedures similar to those described in Example XXI (Parts A and B), except that 3-carbamoyl-1,2,4-triazole-5-thiol was the appropriate starting thiol used instead of 3-carboxymethoxymethyl-1,2,4-triazole-5-thiol. In this particular case, the final product was characterized by both infrared absorption spectroscopy and nuclear magnetic resonance data.

EXAMPLE XXIII 7-(D-α-Amino-p-hydroxyphenylacetamido)-3-(carbamoylmethoxymethyl-1,2,4-triazol-5-yl)thiomethylceph-3-em-4-carboxylic Acid as the Trifluoroacetate Salt This product was prepared by employing procedures similar to those described in Example XXI (Parts A and B), except that 3-carbamoylmethoxymethyl-1,2,4-triazole-5-thiol was the appropriate starting thiol used instead of 3-carboxymethoxymethyl-1,2,4-triazole-5-thiol. In this particular case, the final product was characterized by both infrared absorption spectroscopy and nuclear magnetic resonance data.

EXAMPLE XXIV 7-(D-α-Hydroxyphenylacetamido)-3-(3-carbamoyl-1,2,4-triazol-5-yl)-thiomethylceph-3-em-4-carboxylic Acid To a solution consisting of 3-acetoxymethyl-7-(D-α-hydroxyphenylacetamido)ceph-3-em-4-carboxylic acid (27.6 g.) and the ammonium salt of 3-carbamoyl-1,2,4-triazole-5-thiol (10 g.) in pH 7.0 phosphate buffer, there was added sufficient aqueous 2 N sodium hydroxide to raise the pH to 7.0. The resulting solution was then heated at 70° C. for a period of three hours. The reaction mixture so obtained was then cooled to room temperature (~25° C.) and acidified with aqueous 2 N hydrochloric acid to pH 2.0. Extraction of the acidified mixture with ethyl acetate and subsequent evaporation of the extract then gave a yellow solid (3.0 g.), which was thereafter found by high pressure liquid chromatography to be about 50% pure and so was discarded. The aqueous portion remaining after the extraction contained a gummy residue, which was subsequently collected in the usual manner, washed well with water and finally triturated with a solution of isopropanol-/ethyl acetate. The residue obtained from this trituration amounted to 15 g., and was found to be about 70% pure by high pressure liquid chromatographic analysis. Evaporation of the isopropanol/ethyl acetate filtrate then gave a solid material (5.7 g.), which was found to be about 80% pure. The latter material was subsequently chromatographed on silica, with a 95% pure sample (as attested to by high pressure liquid chromatography) being obtained by elution with a 6% solution of methanol in chloroform. The yield of pure (95%) product amounted to 1.56 g. of pure 7-(D-α-hydroxyphenylacetamido)-3-(3-carbamoyl-1,2,4-triazol-5-yl)thiomethylceph-3-em-4-carboxylic acid, which was further characterized by nuclear magnetic resonance and infrared absorption spectroscopy.

EXAMPLE XXV 7-(D-α-Hydroxyphenylacetamido)-3-(3-Carboxymethoxymethyl-1,2,4-triazol-5-yl)thiomethylceph-3-em-4-carboxylic Acid This product was prepared by employing the procedure essentially described in Example XXIV, except that 3-(carboxymethoxymethyl)-1,2,4-triazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXVI 7-(D-α-Hydroxyphenylacetamido)-3-(2-carbamoylmethoxymethyl-1,3,4-thiadiazole-5-yl)thiomethylceph-3-em-4-carboxylic Acid This product was prepared by employing the procedure essentially described in Example XXIV, except that 2-(carbamoylmethoxymethyl)-1,3,4-thiadiazole-5-thiol was the appropriate starting thiol used in place of 3-carbamoyl-1,2,4-thiazole-5-thiol. In this particular case, the final product was characterized by both infrared absorption spectroscopy and nuclear magnetic resonance data.

EXAMPLE XXVII 7-(D-α-Hydroxyphenylacetamido)-3-(2-ethoxycarbonylmethoxymethyl-1,3,4-thiadiazole-5-yl)thiomethylceph-3-em-4-carboxylic Acid This product was prepared by employing the procedure essentially described in Example XXIV, except that 2-(ethoxycarbonylmethoxymethyl)-1,3,4-thiadiazole-5-thiol was the appropriate starting thiol used in place of 3-carbamoyl-1,2,4-thiazole-5-thiol. In this particular case, the final product was characterized by both infrared absorption spectroscopy and nuclear magnetic resonance data.

EXAMPLE XXVIII 7-(D-α-Hydroxyphenylacetamido)-3-(3-carbamoylmethoxymethyl-4-methyl-1,2,4-triazol-5-yl)thiomethylceph-3-em-4-carboxylic Acid This product was prepared by employing the procedure essentially described in Example XXIV, except that 3-(carbamoylmethoxymethyl)-4-methyl-1,2,4-triazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXIX 7-(D-α-Hydroxyphenylacetamido)-3-(3-carboxymethoxymethyl-4-methyl-1,2,4-triazol-5-yl)thiomethylceph-3-em-4-carboxylic Acid This product was prepared by employing the procedure essentially described in Example XXIV, except that 3-(carboxymethoxymethyl)-4-methyl-1,2,4-triazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXX 7-(D-α-Hydroxyphenylacetamido)-3-(2-carboxymethoxymethyl-1,3,4-oxadiazol-5-yl)thiomethylceph-3-em-4-carboxylic Acid This product was prepared by employing the procedure essentially described in Example XXIV, except that 2-(carboxymethoxymethyl)-1,3,4-oxadiazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXXI 7-(D-α-Hydroxyphenylacetamido)-3-(3-carbamoyl-4-methyl-1,2,3,4-triazolyl-5-yl)thiomethylceph-3-em-4-carboxylic Acid This product was prepared by employing the procedure essentially described in Example XXIV, except that 3-carbamoyl-4-methyl-1,2,4-triazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXXII 7-(D-α-Hydroxyphenylacetamido)-3-(2-carboxymethoxymethyl-1,3,4-thiadiazol-5-yl)thiomethylceph-3-em-4-carboxylic Acid This product was prepared by employing the procedure essentially described in Example XXIV, except that 2-(carboxymethoxymethyl)-1,3,4-thiadiazole-5-thiol was the appropriate starting thiol used in place of 3-carbamoyl-1,2,4-triazole-5-thiol. In this particular case, the final product was characterized by both infrared absorption spectroscopy and nuclear magnetic resonance data.

EXAMPLE XXXIII

Part A

7-Amino-3-(3-carbamoyl-1,2,4-triazol-5-yl)thiomethylceph-3-em-4-carboxylic Acid

7-Formamidocephalosporanic acid (100 g.) was dissolved in pH 7.0 phosphate buffer (1600 ml.) and the pH was adjusted to pH 7.0 with 2 N aqueous sodium hydroxide solution. 3-Carbamoyl-1,2,4-triazole-5-thiol (48 g.) was then added and the pH was again adjusted to 7.0 with 2 N aqueous sodium hydroxide solution. The resulting mixture was next heated at 70° C. for a period of five hours and then cooled to room temperature (~25° C.), and the pH of the resulting solution was subsequently adjusted to pH 0.5 with concentrated hydrochloric acid. The acidified reaction mixture was next diluted with methanol (1500 ml.) and stirred at room temperature for a period of three hours before being cooled to 50° C. The pH was then adjusted to 3.9 with ammonium hydroxide solution and after stirring for two hours at 5° C., the resulting precipitate of 7-amino-3-(3-carbamoyl-1,2,4-triazol-5-yl)thiomethylceph-3-em-4-carboxylic acid (47.9 g.) was filtered off, washed with water, then with acetone and diethyl ether, and finally dried in vacuo at room temperature.

Part B

7-(D-α-Hydroxyphenylacetamido)-3-(3-carbamoyl-1,2,4-triazol-5-yl)thiomethylceph-3-em-4-carboxylic Acid To a solution consisting of 7-Amino-3-(3-carbamoyl-1,2,4-triazol-5-yl)thiomethylceph-3-em-4-carboxylic acid (45 g.) [prepared as described in Part A] and sodium bicarbonate (27 g.) in water (720 ml.) and acetone (600 ml.) at 0° C., there was added D-O-(dichloroacetyl mandeloyl chloride (72 g.) in acetone (120 ml.) over a period of 45 minutes. The pH was maintained at 7.5 throughout the addition step by suitable adjustment with 2 N aqueous sodium hydroxide solution. The reaction mixture was then allowed to warm to room temperature (~25° C.) and stirred for a period of one hour. The acetone solvent was next removed under vacuum, the pH raised to 9.5 by the addition of aqueous sodium carbonate solution and, after a period of 30 minutes, the pH was readjusted to pH 2.0 with concentrated hydrochloric acid. The acidified reaction mixture was then extracted with a mixture of tetrahydrofuran (310 ml.) and ethyl acetate (310 ml.). The organic phase so obtained was separated, washed with water and saturated aqueous sodium chloride and subsequently evaporated to dryness. The residual oil was then triturated with diethyl ether to give pure 7-(D-α-hydroxyphenylacetamido)-3-(3-carbamoyl-1,2,4-triazol-5-yl)-thiomethylceph-3-em-4-carboxylic acid as an off-white solid (yield, 23.3 g.), subsequently confirmed by high pressure liquid chromotography to be identical with the product of Example XXIV.

EXAMPLE XXXIV

7-(D-α-Hydroxyphenylacetamido)-3-(2-carbamoyl-1,3,4-oxadiazol-5-yl)thiomethylceph-3-em-4-carboxylic Acid By employing a procedure similar to that described in Example XXXIII, Part B, 7-(D-α-hydroxyphenylacetamido)-3-(2-carbamoyl-1,3,4-oxadiazol-5-yl)thiomethylceph-3-em-4-carboxylic acid was prepared from 7-amino-3-(2-carbamoyl-1,3,4-oxadiazol-5-yl)thiomethylceph-3-em-4-carboxylic acid and D-O-(formyl)mandeloyl chloride. The final product was characterized by nuclear magnetic resonance and infrared absorption spectroscopy.

EXAMPLE XXXV

Part A

7-Amino-3-(2-carbamoyl-1,3,4-oxadiazol-5-yl)thiomethylceph-3-em-4-carboxylic Acid.

Separate solutions of 7-aminocephalosporanic acid (5.44 g.) and 2-carbamoyl-1,3,4-oxadiazole-5-thiol (3.19 g.) in dilute aqueous sodium hydroxide at pH ca. 7.0, respectively, were mixed (total volume about 75 ml.), and the resulting mixture was stirred and heated in a water-bath at 70° C. for a period of one hour. During the course of the reaction, the pH of the reaction solution was maintained at pH 6.5–7.0 by the addition of aqueous 2 N sodium hydroxide solution. Upon completion of this step, the reaction mixture was cooled rapidly to room temperature (~25° C.) and sufficient 2 N aqueous hydrochloric acid was added to adjust the pH value to 3.5. The resulting brown precipitate was then collected by means of filtration and the product, viz., 7-amino-3-(2-carbamoyl-1,3,4-oxadiazol-5-yl)thiomethyl-ceph-3-em-4-carboxylic acid, was washed well with acetone to yield a tan powder (yield, 3.1 g.).

Part B

7-(D-α-tert-Butoxycarbonylamino)phenylacetamido-3-(2-carbamoyl-1,3,4-oxadiazol-5-yl)thiomethylceph-3-em-4-carboxylic Acid D-N-tert.-Butoxycarbonylphenylglycine (1.9 g.) was dissolved in dry tetrahydrofuran (25 ml.) and the resulting solution cooled to 5° C. Triethylamine (0.76 g.) was then added with stirring, with the resulting reaction mixture subsequently being cooled to −10° C. and treated over a period of two minutes with isobutyl chloroformate (1.0 g.). The resulting solution of the mixed anhydride was then further stirred at −10° C. for a period of 15 minutes.

The cephalosporin product of Part A (1.8 g.) was added to an ice-cold solution of tetrahydrofuran (13 ml.) and water (13 ml.) containing triethylamine (0.5 g.) and then stirred to effect further solution. The resulting solution was next added with to the previously prepared solution of the mixed anhydride at −5° C. during the course of a period of seven minutes. After an additional period of stirring for 30 minutes at this same temperature, the reaction mixture was allowed to stand for two hours during which time the coolant was removed. Water (25 ml.) was then added to the mixture and the resulting aqueous solution extracted once with ethyl acetate. The ethyl acetate extract was next dried over anhydrous magnesium sulfate and evaporated in vacuo to afford a product that was subsequently triturated with dry diethyl ether to yield an off-white solid (yield, 530 mg.) The saved aqueous phase was then overlayered with ethyl acetate, the pH subsequently adjusted to pH 2.0 by the addition of aqueous 2 N hydrochloric acid and the organic layer thereafter separated and dried over anhydrous magnesium sulfate. The organic solvent was then evaporated in vacuo and the product triturated with dry diethyl ether to yield another off-white solid (yield 800 mg.) Inasmuch as thin layer chromatographic analysis subsequently revealed both crops to be identical, i.e., pure 7-(D-α-tert-butoxycarbonylamino)phenylacetamido-3-(2-carbamoyl-1,3,4-oxadiazol-5-yl)thiomethylceph-3-em-4-carboxylic acid, they were combined to afford a total yield of 1.33 g. of desired product.

Part C

7-(D-α-Aminophenylacetamido)-3-(2-carbamoyl-1,3,4-oxadiazol-5-yl)thiomethylceph-3-em-4-carboxylic Acid as the Trifluoroacetate Salt The product from Part B (500 mg.) was added with stirring to ice-cold trifluoroacetic acid (5 ml.). After a period of six minutes, the brown solution was evaporated in vacuo and the oily residue subsequently triturated with dry diethyl ether. The resulting solid, viz., the trifluoroacetic acid salt of 7-(D-α-aminophenylacetamido)-3-(2-carbamoyl-1,3,4-oxadiazol-5-yl)thiomethylceph-3-em-4-carboxylic acid, was recovered by means of filtration, washed well with dry diethyl ether and dried in vacuo. The yield of off-white material was 500 mg.

Part D

7-(D-α-Aminophenylacetamido)-3-(2-carbamoyl-1,3,4-oxadiazol-5-yl)thiomethylceph-3-em-4-carboxylic Acid To obtain the zwitter-ionic form of the desired product, the trifluoroacetate salt prepared as in Part C above (400 mg.) was suspended in water (5 ml.) and the pH of the resulting mixture was adjusted to 7.5 by the addition of aqueous 2 N sodium hydroxide solution. The resulting solution was then filtered to remove insoluble material and the pH of the filtrate adjusted to 3.5 by addition of aqueous 2 N hydrochloric acid. After standing for two days at 5° C., the product, viz., 7-(D-α-aminophenylacetamido)-3-(2-carbamoyl-1,3,4-oxadiazol-5-yl)thiomethylceph-3-em-4-carboxylic acid in zwitter-ionic form, was collected by filtration, washed with a little water and dried in vacuo. The yield of off-white solid material was 100 mg. The product was characterized by means of thin layer chromatography, as well as infrared absorption and nuclear magnetic resonance spectroscopy.

EXAMPLE XXXVI

7-(D-α-Amino-p-hydroxyphenylacetamido)-3-(2-carbamoyl-1,3,4-oxadiazol-5-yl)thiomethylceph-3-em-4-carboxylic Acid This product was prepared by employing procedures similar to those already described in Example XXXV (Parts A-D), starting from 7-aminocephalosporanic acid and 2-carbamoyl-1,3,4-oxadiazole-5-thiol, and using N-tert.-butoxycarbonyl-p-hydroxyphenylglycine as the appropriate reagent of choice in Part B. In this particular case, the final product was ultimately isolated in zwitter-ionic form (after conversion of the trifluoroacetate salt) and was subsequently characterized by means of infrared absorption spectroscopy.

Example XXXVII

7-(D-α-Aminophenylacetamido)-3-(2-N-methylcarbamoyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(N-methylcarbamoyl)-1,3,4-oxadiazole-5-thiol, and using N-tert.-butoxycarbonylphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XXXVIII

7-(D-α-Aminophenylacetamido)-3-(2-N,N-dimethylcarbamoyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(N,N-dimethylcarbamoyl)-1,3,4-oxadiazole-5-thiol, and using N-tert.-butoxycarbonylphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XXXIX

7-(D-α-Amino-p-hydroxyphenylacetamido)-3-(2-N,N-dimethylcarbamoyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(N,N-dimethylcarbamoyl)-1,3,4-oxadiazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XL

7-D-α-Aminophenylacetamido)-3-(2-N-ethylcarbamoyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(N-ethylcarbonyl)-1,3,4-oxadiazole-5-thiol, and using N-tert.-butoxycarbonylphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLI

7-(D-α-Amino-p-hydroxyphenylacetamido)-3-(2-N-ethylcarbamoyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(N-ethylcarbamoyl)-1,3,4-oxadiazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by infrared absorption spectroscopy.

EXAMPLE XLII

7-(D-α-Amino-p-hydroxyphenylacetamido)-3-(2-ethoxycarbonylmethoxymethyl-1,3,4-oxadiazol-5-yl)thiomethylceph-3-em-4-carboxylic Acid This product was prepared by employing procedures similar to those already described in Example XXXV (Parts A-C), starting from 7-aminocephalosporanic acid and 2-(ethoxycarbonylmethoxymethyl-1,3,4-oxadiazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLIII

7-D-Aminophenylacetamido)-3-(2-N-methylcarbamoyl-1,3,4-thiadiazol-5-yl)thiomethylceph-3-em-4-carboxylic Acid This product was prepared by employing procedures similar to those already described in Example XXXV (Parts A–C), starting from 7-aminocephalosporanic acid and 2-(N-methylcarbamoyl)-1,3,4-thiadiazol-5-thiol, and using N-tert.-butoxycarbonylphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLIV 7-(D-α-Aminophenylacetamido)-3-(3-carbamoyl-4-methyl-1,2,4-triazol-5-yl)thiomethylceph-3-em-4-carboxylic Acid This product was prepared by employing procedures similar to those already described in Example XXXV (Parts A–C), starting from 7-aminocephalosporanic acid and 3-carbamoyl-4-methyl-1,2,4-triazole-5-thiol, and using N-tert.-butoxycarbonylphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLV 7-(D-α-Amino-p-hydroxyphenylacetamido)-3-(3-carbamoyl-4-methyl-1,2,4-triazol-5-yl)thiomethylceph-3-em-4-carboxylic Acid This product was prepared by employing procedures similar to those already described in Example XXXV (Parts A–C), starting from 7-aminocephalosporanic acid and 3-carbamoyl-4-methyl-1,2,4-triazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLVI 7-(D-α-Amino-p-hydroxyphenylacetamido)-3-(3-ethoxycarbonylmethoxymethyl-4-methyl-1,2,4-triazol-5-yl)thiomethylceph-3-em-4-carboxylic Acid This product was prepared by employing procedures similar to those already described in Example XXXV (Parts A–C), starting from 7-aminocephalosporanic acid and 3-(ethoxycarbonylmethoxymethyl)-4-methyl-1,2,4-triazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLVII 7-(D-α-Amino-p-hydroxyphenylacetamido)-3-(3-carboxymethoxymethyl-4-methyl-1,2,4-triazol-5-yl)thiomethylceph-3-em-4-carboxylic Acid This product was prepared by employing procedures similar to those already described in Example XXXV (Parts A–C), starting from 7-aminocephalosporanic acid and 3-(carboxymethoxymethyl)-4-methyl-1,2,4-triazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLVIII 7-(D-α-Amino-p-hydroxyphenylacetamido)-3-(2-carboxymethoxymethyl-1,3,4-thiadiazol-5-yl)thiomethylceph-3-em-4-carboxylic Acid This product was prepared by employing procedures similar to those already described in Example XXXV (Parts A–C), starting from 7-aminocephalosporanic acid and 2-(carboxymethoxymethyl)-1,3,4-thiadiazole-5-thiol, and using N-tert.-butoxycarbonyl-p-hydroxyphenylglycine as the appropriate reagent of choice in Part B. In this particular case, the final product was isolated as the trifluoroacetate salt and was subsequently characterized by both infrared absorption spectroscopy and nuclear magnetic resonance data.

EXAMPLE XLIX

Part A (D)-5-Phenyl-1,3-dioxolan-2,4-dione

A solution of phosgene (56.9 g.) in toluene (500 ml.) was added over a one hour period to (D)-α-hydroxyphenylacetic acid (45.6 g.) dissolved in tetrahydrofuran (450 ml.) at room temperature (~25° C.) and the resulting mixture was then heated at 75° C. for a period of six hours. The organic solvent was next removed under vacuum and the residue was crystallized from carbon tetrachloride to afford pure (D)-5-phenyl-1,3-dioxolan-2,4-dione as a white solid (yield, 49.4 g.), m.p. 76°–77° C.

Analysis: Found: C, 60.37; H, 3.68%. Calcd. for $C_9H_6O_4$: C, 60.67; H, 3.39%.

Part B 7-(D-α-Hydroxyphenylacetamido)-3-(3-carbamoyl-1,2,4-triazol-5-yl)thiomethylceph-3-em-4-carboxylic Acid (D)-5-Phenyl-1,3-dioxolan-2,4-dione (50.4 g.) was added over a period of 15 minutes to a solution of 7-amino-3-(3-carbamoyl-1,2,4-triazol-5-yl)thiomethylceph-3-em-4-carboxylic acid (84.0 g.) in aqueous phosphate buffer (1075 ml.) at pH 6.8. The resulting solution was then stirred for 45 minutes at room temperature (~25° C.), a mixture of ethyl acetate and tetrahydrofuran (1:1 by volume; 840 ml.) was added and the pH of the aqueous phase subsequently reduced to pH 2.0 with concentrated hydrochloric acid. The organic layer was then separated, washed with water (800 ml.) and thereafter dried and evaporated under reduced pressure. Trituration of the resulting residue with diethyl ether then gave the crude product as a pale yellow solid (80.2 g.). Subsequent chromatography on silica using up to 10% methanol in chloroform as eluant finally yielded the pure product, viz., 7-(D-α-hydroxyphenylacetamido)-3-(3-carbamoyl-1,2,4-triazol-5-yl)thiomethylceph-3-em-4-carboxylic acid, which was found to be chromatographically and spectroscopically identical with the material earlier prepared according to the procedure described in Example XXIV.

EXAMPLE L

Diphenylmethyl 7-(D-α-Hydroxyphenylacetamido)-3-(3-carbamoyl-1,2,4-triazol-5-yl)thiomethylceph-3-em-4-carboxylate The product of Example XXIV (100 mg.) was added to an ice-cooled, stirred solution of diphenyl diazomethane (45.1 mg.) in ethyl acetate (15 ml.), and the resulting reaction mixture was kept under refrigeration for a period of about 20 hours. The cooled mixture was then washed with aqueous sodium bicarbonate solution and then with water, followed by separation of the organic layer which was subsequently dried over magnesium sulfate. The dried organic layer was then evaporated in vacuo and the residue triturated with dry diethyl ether to give the diphenylmethyl ester of 7-(D-α-hydroxyphenylacetamido)-3-(3-carbamoyl-1,2,4-triazol-5-yl)thiomethylceph-3-em-4-carboxylic acid as a white solid (yield, 99 mg.), m.p. 133°–135° C. A portion of this material was recrystallized from isopropanol to provide the analytical sample.

Analysis: Found: C, 58.56; H, 4.32%. Calcd. for $C_{32}H_{28}N_6O_6S_2$: C, 58.52; H, 4.30%.

The final product was also characterized by means of infrared absorption spectroscopy.

EXAMPLE LI 7-(D-α-Formyloxyphenylacetamido)-3-(3-carbamoyl-1,2,4-triazol-5-yl)thiomethylceph-3-em-4-carboxylic Acid N,O-Bis(trimethylsilyl)acetamide (800 mg.) was added to a suspension of the product of Example XXXIII, Part A (400 mg.) in dry tetrahydrofuran (9 ml.) and the resulting mixture was warmed at 50° C. for a period of 20 minutes, after which time a clear solution was obtained. This solution was then cooled to room temperature (~25° C.), and a solution consisting of D-O-formylmandeloyl chloride (0.23 g.) [prepared as described in German Offenlegungschrift No. 2,506,622] dissolved in dry tetrahydrofuran (1.0 ml.) was thereafter added. After stirring for a period of two hours, ethyl acetate (10 ml.) and water (5 ml.) were subsequently added and this final mixture was further stirred for a period of ten minutes. The organic phase was then separated, washed twice with water, separated and subsequently dried over anhydrous magnesium sulfate. Evaporation of the dried filtrate in vacuo then gave 0.5 g. of crude material. Trituration of the latter material with dry acetone finally afforded pure product viz., 7-(D-α-formyloxyphenylacetamido)-3-(3-carbamoyl-1,2,4-triazol-5-yl)thiomethylceph-3-em-4-carboxylic acid, as an off-white solid (yield, 140 mg.). The final product was characterized by ultraviolet and infrared absorption spectroscopy, as well as nuclear magnetic resonance data.

EXAMPLE LII

Pivalyloxymethyl-7-(D-α-Hydroxyphenylacetamido)-3-(3-carbamoyl-1,2,4-triazol-5-yl)thiomethylceph-3-em-4-carboxylate Sodium bromide (28 mg.) was added to a stirred solution of the chloromethyl ester of pivalic acid (40 mg.) dissolved in dry dimethylformamide (1.5 ml.). After a period of 15 minutes, the product of Example XXIV (123 mg.) was added and after a further ten minutes, a solution of dicyclohexylamine (50 mg.) in dry dimethylformamide (0.5 ml.) was added dropwise. The latter step required a period of approximately 15 minutes. The resulting reaction mixture was then stirred for 17 hours at room temperature (~25° C.), after which time water and ethyl acetate were added. The organic layer was subsequently separated and washed successively with separate portions of aqueous sodium bicarbonate, water, aqueous 1 N hydrochloric acid and water. After drying over anhydrous magnesium sulfate, the solvent was removed in vacuo and the residue triturated with dry diethyl ether to afford the pure product, viz., pivalyloxymethyl 7-(D-α-hydroxyphenylacetamido)-3-(3-carbamoyl-1,2,4-triazol-5-yl)thiomethylceph-3-em-4-carboxylate, as an off-white solid (yield, 34 mg.). The final product was characterized by infrared absorption spectroscopy and nuclear magnetic resonance data.

What is claimed is:

1. A compound of the formula:

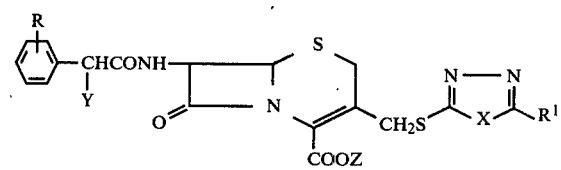

and the pharmaceutically acceptable salts thereof, wherein

R is a member selected from the group consisting of hydrogen and hydroxyl;

Y is a member selected from the group consisting of amino and $OR^4$ where $R^4$ is chosen from the group consisting of lower alkanoyl, lower alkoxycarbonyl and benzoyl;

Z is a member selected from the group consisting of hydrogen, lower alkyl, benzhydryl, phenyl, indan-5-yl, lower alkylcarbonyloxymethyl, lower α-(alkoxycarbonyloxy)ethyl and 3-phthalido;

$R^1$ is a member selected from the group consisting of carboxymethoxymethyl, lower alkoxycarbonylmethoxymethyl and $CH_2OCH_2CONR^2R^3$ wherein $R^2$ and $R^3$ are each chosen from the group consisting of hydrogen and lower alkyl; and X is a member selected from the group consisting of oxygen, sulfur, imino and N-methylimino.

2. A compound as claimed in claim 1 wherein Y is amino and Z is hydrogen.

3. A compound as claimed in claim 1 wherein R is p-hydroxyl, Y is amino and Z is hydrogen.

4. A compound as claimed in claim 1 wherein R is p-hydroxyl, Y is amino, Z is hydrogen and $R^1$ is carboxymethoxymethyl.

5. A compound as claimed in claim 1 wherein R is p-hydroxyl, Y is amino, Z is hydrogen and $R^1$ is $CH_2OCH_2CONR^2R^3$ wherein $R^2$ and $R^3$ are each hydrogen.

6. A compound as claimed in claim 1 wherein R is p-hydroxyl, Y is amino, Z is hydrogen, $R^1$ is carboxymethoxymethyl and X is imino.

7. A pharmaceutical composition comprising a compound as claimed in claim 1 and a pharmaceutically acceptable carrier.

8. A method for treating an animal of diseases caused by Gram-positive and Gram-negative bacteria, which comprises administering to said animal an antibacterially effective amount of a compound as claimed in claim 1.

* * * * *